US00PP23894P2

(12) United States Plant Patent
Bourne

(10) Patent No.: US PP23,894 P2
(45) Date of Patent: Sep. 10, 2013

(54) ***DIANTHUS* PLANT NAMED 'WP10 VEN06'**

(50) Latin Name: *Dianthus×hybrida*
Varietal Denomination: WP10 VEN06

(76) Inventor: Carolyn Grace Bourne, Dawlish (GB)

( * ) Notice: Subject to any disclaimer, the term of this patent is extended or adjusted under 35 U.S.C. 154(b) by 358 days.

(21) Appl. No.: 13/065,394

(22) Filed: Mar. 22, 2011

(51) Int. Cl.
*A01H 5/00* (2006.01)

(52) U.S. Cl.
USPC ..... Plt./279

(58) Field of Classification Search
USPC ..... Plt./279
See application file for complete search history.

(56) References Cited

U.S. PATENT DOCUMENTS

| | | | | |
|---|---|---|---|---|
| PP12,670 | P2 * | 6/2002 | Klemm | Plt./279 |
| PP20,080 | P2 * | 6/2009 | van der Helm | Plt./279 |
| PP21,596 | P2 * | 12/2010 | Breier | Plt./279 |
| 2011/0321206 | P1 * | 12/2011 | Bourne | Plt./279 |

* cited by examiner

*Primary Examiner* — Wendy C Haas

(57) ABSTRACT

A new cultivar of *Dianthus* plant named 'WP10 VEN06' which is characterized by cold tolerance, compact habit, glaucous foliage and fragrant double white flowers. In combination, these characteristics set 'WP10 VEN06' apart from all other existing varieties of *Dianthus* known to the inventor.

2 Drawing Sheets

Genus: *Dianthus.*
Species: ×*hybrida.*
Denomination: 'WP10 VEN06'.

BACKGROUND OF THE INVENTION

The present invention relates to a new and distinct cultivar of hardy garden pink or carnation that is grown for use as a flowering plant for pots and containers and for planting in the garden and landscape. The new cultivar is known botanically as *Dianthus×hybrida* and will be referred to hereinafter by the cultivar name 'WP10 VEN06'.

'WP10 VEN06' is a complex hybrid plant that is the product of a breeding program started by the inventor in 1985. The breeding program is conducted in a cultivated area of Houndspool, Dawlish, Devon, United Kingdom. The inventor selected 'WP10 VEN06' in 2004 for its fragrant flowers which are double and white in color.

'WP10 VEN06' resulted from the controlled pollination between two unreleased and unpatented selections of *Dianthus* from the inventor's breeding program, namely Selection 'Noelle' (unpatented and unreleased) as male parent and Selection 'ASH2' (unpatented and unreleased) as female parent.

'WP10 VEN06' is distinguishable from both parents by flower color. Whereas the flowers of 'WP10 VEN06' are double and white in color, the flowers of the male parent are double and carmine in color and the flowers of the female parent are semi-double and carmine in color.

The variety of *Dianthus* which is considered by the inventor to most closely resemble 'WP10 VEN06' is the inventor's variety *Dianthus* 'Arctic Star' (unpatented). The flowers of 'Arctic Star' are similarly double and white in color. However, the foliage of 'Arctic Star' is less glaucous than the foliage of 'WP10 VEN06'. In addition, 'Arctic Star' has been found to be less hardy than other *Dianthus* varieties from the inventor's breeding program including 'WP10 VEN06'.

Asexual reproduction of 'WP10 VEN06' was first accomplished by the inventor in 2004 in a cultivated area of Houndspool, United Kingdom. The method of asexual propagation used was vegetative cuttings. The inventor has determined that 'WP10 VEN06' is stable and reproduces true to type in successive generations of asexual propagation.

SUMMARY OF THE INVENTION

The following traits have been repeatedly observed and represent the characteristics of the new *Dianthus* cultivar 'WP10 VEN06'. These traits in combination distinguish this cultivar from all other commercial varieties known to the inventor. 'WP10 VEN06' has not been tested under all possible conditions and phenotypic differences may be observed with variations in environmental, climatic and cultural conditions, however, without any variance in genotype.

1. *Dianthus* 'WP10 VEN06' exhibits a compact habit.
2. The flowers of *Dianthus* 'WP10 VEN06' are double.
3. The flowers of *Dianthus* 'WP10 VEN06' are white in color.
4. *Dianthus* 'WP10 VEN06' blooms from April through October.
5. *Dianthus* 'WP10 VEN06' exhibits glaucous grey-green foliage.
6. At nine months of age, the height of the foliage mound of *Dianthus* 'WP10 VEN06' is 20 cm to 24 cm, and the width is 10 cm to 13 cm.
7. *Dianthus* 'WP10 VEN06' is perennial and is hardy to −15° C.
8. *Dianthus* 'WP10 VEN06' is suitable for use as a flowering plant in pots and containers.

BRIEF DESCRIPTION OF THE DRAWINGS

The accompanying color drawings illustrate the overall appearance of the new *Dianthus* variety 'WP10 VEN06' showing colors as true as it is reasonably possible to obtain in colored reproductions of this type. Colors in the drawings may differ from the color values cited in the detailed botanical description, which accurately describe the actual colors of the new variety 'WP10 VEN06'.

The drawing labeled as FIG. 1 depicts an entire flowering plant of 'WP10 VEN06'.

Figure 1:
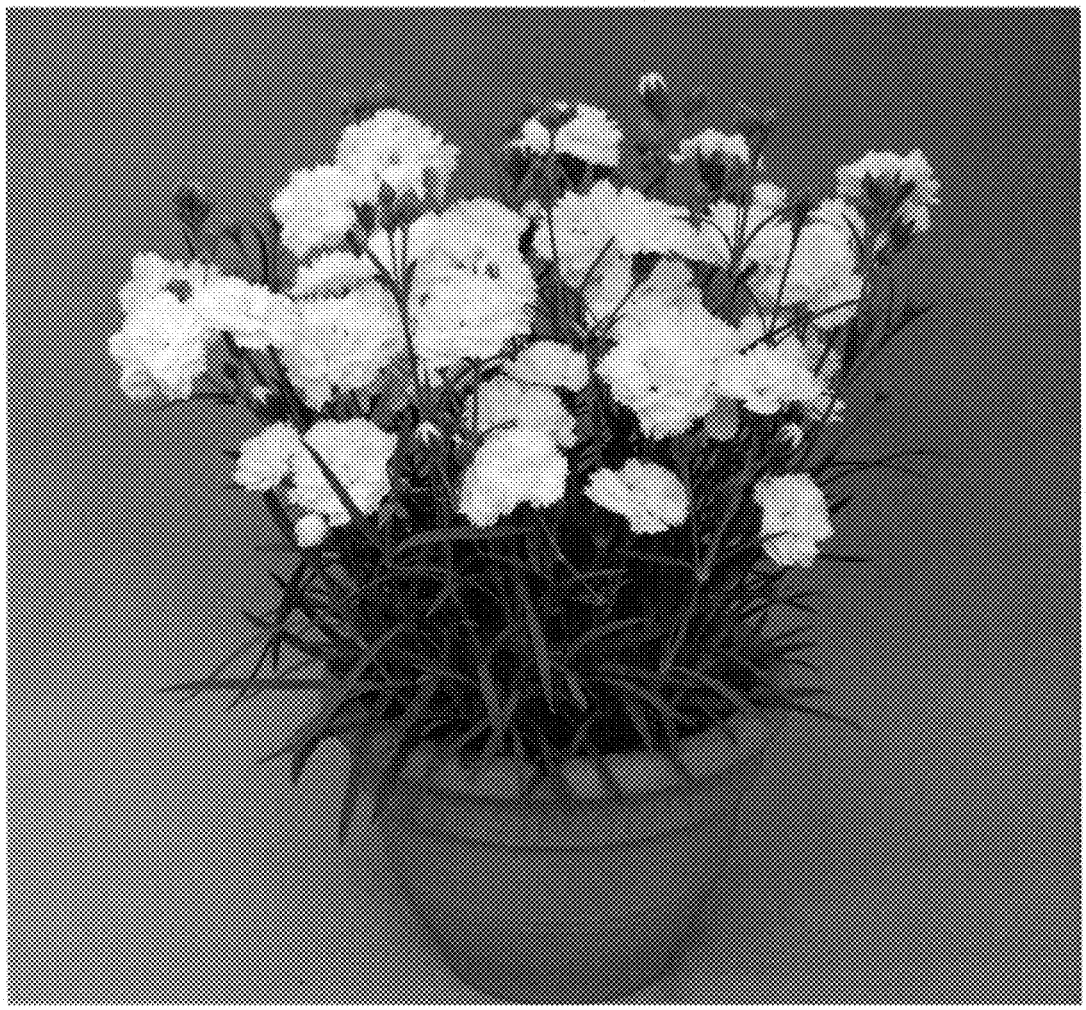
Figure 2:
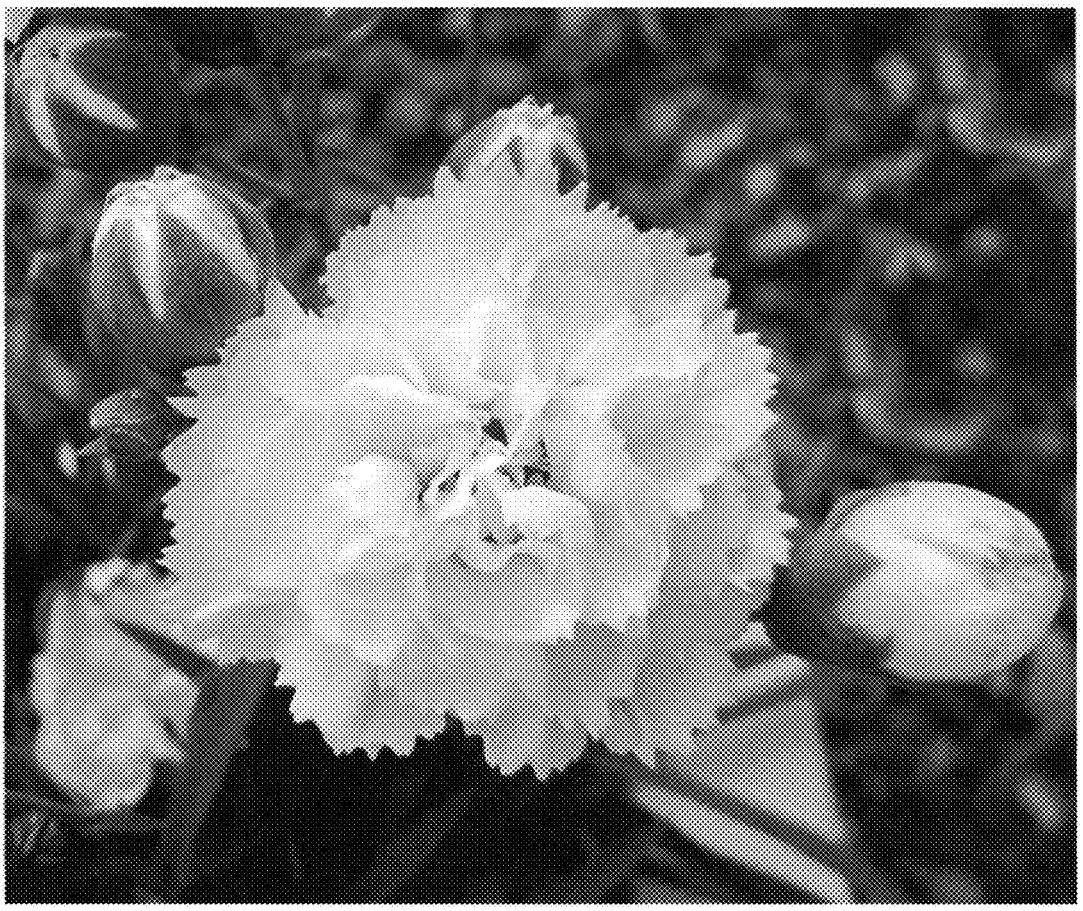

The drawing labeled as FIG. 2 depicts a close-up view of the flower of 'WP10 VEN06'.

All drawings were made from 9 months old plants which have been grown in 1.5-litre containers in a cold glasshouse in Devon, United Kingdom. No chemicals were used to treat the plants. All drawings were made using conventional techniques and although colors may appear different from actual colors due to light reflectance they are as accurate as possible by conventional photography.

DETAILED BOTANICAL DESCRIPTION OF THE PLANT

The following is a detailed description of the new cultivar 'WP10 VEN06'. Data was collected in spring from 1.5-litre container plants in spring, and grown indoors in Devon, United Kingdom. The color determinations are in accordance with the 2001 edition of The Colour Chart of the Royal Horticultural Society, London, England, except where general color terms of ordinary dictionary significance are used. The colors of stems, leaves, calyx, and epicalyx have been noted on plants which retain the characteristic waxy bloom of *Dianthus*. No chemicals were used to treat the plants. Growing conditions are typical to other *Dianthus*.

Botanical classification:
- *Family*.—Caryophyllaceae.
- *Genus*.—*Dianthus*.
- *Species*.—×*hybrida*.
- *Denomination*.—'WP10 VEN06'.

Parentage: A complex *Dianthus* hybrid whose immediate parents are unreleased hybrids from the inventor's breeding program, identified as follows:
- *Male parent*.—Unpatented selection of *Dianthus* from the inventor's breeding program, known as Selection "Noelle".
- *Female parent*.—Unpatented selection of *Dianthus* from the inventor's breeding program, known as Selection "ASH2".

Plant type: Flowering perennial.

Use of plant: As a flowering plant in containers, window boxes, planters, pots and the garden.

Bloom period: April-October in Devon, UK.

Plant habit: A compact mound with many branches and stems upright.

Height of plant: 20 cm to 24 cm after 9 months.

Width of plant: 10 cm to 13 cm after 9 months.

Hardiness: Has survived in temperatures of minus 15 Centigrade, equivalent to USDA Hardiness Zone 7.

Root system: Many fibrous roots.

Propagation method: Vegetative stem cuttings.

Cultural requirements: Grow in full sun, in well drained and moderately fertile soil, keep well fertilized and watered.

Diseases and pests: No particular resistance or susceptibility to *Dianthus* diseases and pests are known to the inventor.

Temperature for rooting: A minimum of 15° C. air temperature and 21° C. base temperature at root level is required to produce roots on the cuttings.

Time to root cuttings: From 2 to 3 weeks is required to produce roots on a vegetative cutting using the rooting temperatures above.

Facilities for rooting: Mist propagation unit is required for satisfactory rooting of cuttings.

Crop time (from planting a rooted cutting): 3 months starting in the Spring and 6 months starting in the Fall.

Plant stem:
- *Shape*.—Cylindrical.
- *Height*.—20 cm to 24 cm.
- *Diameter*.—5 mm to 7 mm.
- *Surface*.—Glabrous and glaucous.
- *Color*.—N189B.
- *Branching*.—Numerous shoots from the axils of the lower leaves.
- *Internode length*.—10 mm-40 mm between nodes.
- *Node dimensions*.—4 mm in diameter and 3 mm in length.

Leaf:
- *Type*.—Evergreen.
- *Dimensions*.—7 cm-9 cm in length and 5-7 mm in width.
- *Shape*.—Linear.
- *Division*.—Simple.
- *Apex*.—Acute
- *Base*.—Decurrent.
- *Venation*.—Not prominent.
- *Margins*.—Entire.
- *Arrangement*.—Opposite and spiraling on stem.
- *Attachment*.—Sheathing.
- *Surface* (*adaxial and abaxial*).—Glaucous.
- *Stipules*.—Absent.
- *Fragrance*.—Absent.
- *Dimensions*.—Length: 100 mm to 150 mm. Width: 4 mm to 5 mm.
- *Color*.—Adaxial surface: 189A. Abaxial surface: N138B.

Inflorescence:
- *Flower stem*.—Length: 8-12 cm. Width: 2-3 mm. Stem strength: Erect. Stem color: N189B.
- *Inflorescence*.—Cymose.
- *Type*.—Salviform, symmetrical.
- *Development*.—Singly, in sequence from the uppermost bud.

Buds:
- *Shape*.—Globular.
- *Dimensions*.—13 mm in length and 10 mm in width.
- *Color*.—Ranges between 136B and 143B.
- *Surface texture*.—Glabrous.

Flowers:
- *Number*.—5 to 7 per stem.
- *Pedicel dimensions*.—8 cm-12 cm length and 2 mm-3 mm in width.
- *Pedicel strength*.—Erect.
- *Pedicel color*.—N189B.
- *Flower dimensions*.—Length (including calyx): 35 to 40 mm. Diameter: 34 mm.
- *Flower shape*.—Circular.
- *Flower profile*.—Reflexed.
- *Lastingness*.—10 days at 20° C., on the plant.
- *Fragrance*.—Moderate, clove-like.
- *Flowering period*.—May to October, in Devon, United Kingdom.

Corolla:
- *Shape* (*upper part of corolla*).—Flat convex.
- *Shape* (*lower part of corolla*).—Concave.

*Petal arrangement*.—Persistent, apopetalous, overlapping.
*Petal margin*.—Serrate.
*Indentation*.—Averages 1 mm in depth.
*Petal texture*.—Soft.
*Flower type*.—Double.
*Petal number*.—Ranges from 35 to 50.
*Petal dimension*.—Length: 35 mm. Width: 15 mm.
*Color of surfaces* (*both upper and lower*).—Ground color of blade: Pure white, whiter than 155D. Color of strap: 144D.
*Petal shape*.—Obdeltoid.
*Petal apex*.—Rounded, slightly flattened.
*Petal base*.—Tapers to narrow base, width at base 2 mm.
*Petal surface*.—Glabrous.

Calyx:
*Shape*.—Cylindrical.
*Sepal apex*.—Subacute.
*Sepal base*.—Fused.
*Longitudinal profile*.—Flat.
*Dimensions*.—Length: 20 mm. Diameter: 6-8 mm.
*Sepals*.—Fused.
*Sepals number*.—5.
*Sepals color*.—Predominantly 136B; 144B or 144C at the apex.
*Anthocyanin*.—Absent.
*Splitting*.—Yes.

Epicalyx:
*Bracts number*.—1 pair of two.
*Shape of outer lobe*.—Acuminate.
*Dimensions*.—Width: 8 mm. Length: 12 mm.
*Color*.—N138A, 144C and 144D are all individually present.
*Anthocyanin*.—Absent.

Bracteoles:
*Number*.—1 pair of 2.
*Dimensions*.—Width: 9 mm. Length: 8 mm.
*Color*.—N138A, 144C and 144D are all individually present.
*Anthocyanin*.—Absent.

Reproductive organs:
*Stamens*.—Number: 10-20.
*Filaments*.—Number: 10 to 20. Color: White.
*Dimensions*.—Length: 20-30 mm in length and 0.5 mm in width.
*Anthers*.—Number: 10 to 20. Color: White. Length: 2 mm; diameter: 0.5-1 mm. Attachment: Dorsifixed.
*Pollen*.—Present.
*Pollen color*.13 N155A.
*Style*.—Number: 2 to 3. Shoulder: Absent. Color: White. Length: 25 mm to 30 mm. Width: 0.5 mm.
*Stigma*.—Number: Single. Color: White to cream. Dimensions: 5 mm above petals at maturity.
*Ovary*.—Position: Superior. Dimensions: Length: 7 mm; diameter: 5 mm. Shape: Rhomboid. Color (upper surface): 143C. Color (lower surface): 145B.
*Seed*.—Seed has not been found during repeated observations.

The invention claimed is:

1. A new and distinct cultivar of *Dianthus* plant named 'WP10 VEN06' as described and illustrated herein.

* * * * *